United States Patent [19]

Ikai et al.

[11] Patent Number: 5,939,573

[45] Date of Patent: Aug. 17, 1999

[54] PROCESS FOR PREPARING DI (POLYCYCLIC AMINO) DIALKOXYSILANE

[75] Inventors: Shigeru Ikai; Yasuhisa Sakakibara; Toshifumi Fukunaga, all of Chiba, Japan

[73] Assignee: Ube Industries, Ltd., Yamaguchi, Japan

[21] Appl. No.: 09/176,539

[22] Filed: Oct. 21, 1998

[30] Foreign Application Priority Data

Oct. 21, 1997 [JP] Japan ..................................... 9-288277

[51] Int. Cl.⁶ ....................................................... C07F 7/10
[52] U.S. Cl. ............................................. 556/413; 546/14
[58] Field of Search ................................ 546/14; 556/413

[56] References Cited

U.S. PATENT DOCUMENTS

| | | | |
|---|---|---|---|
| 3,340,286 | 9/1967 | Schiefer et al. | 556/413 |
| 4,045,460 | 8/1977 | Kleinstuck | 556/413 |
| 5,001,246 | 3/1991 | Ishimura et al. | 556/413 |

*Primary Examiner*—Paul F. Shaver
*Attorney, Agent, or Firm*—McAulay Nissen Goldberg Kiel & Hand, LLP

[57] ABSTRACT

A di(polycyclic amino)dialkoxysilane which is of value as an auxiliary catalyst component for polymerizing an α-olefin to produce an α-olefin polymer having a high stereoregularity and a broad molecular weight distribution is prepared by reacting a secondary polycyclic-amine compound with an organomagnesium compound in an ether solvent, to produce a polycyclic-amido magnesium compound, and reacting the polycyclic-amido magnesium compound with a tetraalkoxysilane in a solvent mixture of an ether solvent and an inert hydrocarbon solvent.

9 Claims, No Drawings

PROCESS FOR PREPARING DI (POLYCYCLIC AMINO) DIALKOXYSILANE

FIELD OF THE INVENTION

The present invention relates to a process for preparing a di(polycyclic amino)dialkoxysilane, which is of value as an auxiliary catalyst component for polymerizing an α-olefin to produce an α-olefin polymer having a high stereoregularity and a broad molecular weight distribution.

BACKGROUND OF THE INVENTION

It is well known that α-olefin is polymerized in the presence of a catalyst composition comprising a solid catalyst components (which comprises magnesium, titanium, halogen, and an internal electron donor), an organoaluminum component and an external electron donor to produce an α-olefin polymer. Recently, it has been found that the stereoregularity of an α-olefin polymer produced by polymerization of α-olefin is enhanced by the use of an aminosilane compound as an auxiliary catalyst component. Until now, there have been reported a number of aminosilane compounds. For instance, Japanese patent provisional publications H3-74393, H7-118320, and H8-100019 describe alkoxy(hydrocarbylamino)dialkoxysilane compounds which are of value as auxiliary catalyst component for the polymerization of α-olefin.

Japanese patent provisional publications H8-120021 and H8-143621 disclose a process of polymerizing α-olefin using a catalyst which contains an aminosilane compound having a cyclic amino group, such as mono(cyclic amino) alkylalkoxysilane and di(cyclic amino)dialkoxysilane.

Japanese patent provisional publication H3-74393 describes a synthesis method of an aminosilane compound which comprises a reaction between an alkyl(trialkoxy) silane and a lithium amide which is prepared by a reaction of an organolithium compound and an amine compound.

The aforementioned Japanese patent provisional publications H8-120021 describes a process for preparing a mono (cyclic amino)alkylalkoxysilane compound by reacting a secondary cyclic amine compound with a halogenated silicon compound or with a Si—O bond-containing silicon compound.

The aforementioned Japanese patent provisional publication H8-143621 describes a process for preparing a di(cyclic amino)dialkoxysilane compound by reacting a secondary cyclic amine compound with a halogenated silicon compound or reacting an alkali or alkaline earth metal salt of a secondary cyclic amine compound with tetraalkoxysilane.

Japanese patent provisional publication H9-67379 describes a process for preparing a diaminodialkoxysilane which comprises a reaction between a tetraalkoxysilane and lithium amide which is produced by reacting a dialkylamine with butyl lithium, or a reaction between a tetraalkoxysilane and a Grinard reagent such as diethylaminomagnesium chloride in diethyl ether.

Research chemists including the present inventors have recently discovered that a catalyst composition comprising a solid catalyst component (which comprises magnesium, titanium, halogen, and an internal electron donor), an organoaluminum component, an external electron donor, and a di(polycyclic amino)dialkoxysilane (auxiliary component) is effective to produce an α-olefin polymer having a high stereoregularity and a broad molecular weight distribution. This discovery is disclosed in U.S. patent application Ser. No. 08/959,302 and EP-A-97402610.

The above-mentioned application documents describe that di(perhydroisoquinolino)dimethoxysilane which is one of the di(polycyclic amino)dialkoxysilanes is obtained by reacting tetramethoxysilane with a lithium salt of perhydroisoquinoline which is produced by reaction between perhydroisoquinoline and butyl lithium. The use of butyl lithium is disadvantageous for an industrial process for the production of bis(perhydroquinoline)dimethoxysilane, because butyl lithium easily ignites. Therefore, the producing process utilizing butyl lithium requires specific care in its handling.

SUMMARY OF THE INVENTION

It is an object of the invention to provide a process for preparing a di(polycyclic amino)dialkoxysilane in a high yield, which requires no specific care in handling starting compounds.

There is provided by the present invention a process for preparing a di(polycyclic amino)dialkoxysilane which comprises the steps of:

reacting a secondary polycyclic amine compound with an organomagnesium compound having a formula of RMgX, wherein R is a hydrocarbyl group and X is a sigma-bonding ligand, in an ether solvent, to produce a polycyclic amido magnesium compound (first step), and reacting the polycyclic amido magnesium compound with a tetraalkoxysilane in a solvent mixture of an ether solvent and an inert hydrocarbon solvent (second step).

The invention resides in an improvement of a process for preparing a di(polycyclic amino)dialkoxysilane which comprises the steps of reacting a secondary polycyclic amine compound with an organomagnesium compound to produce a polycyclic amido magnesium compound (or polycyclic amino magnesium compound) and reacting the produced polycyclic amido magnesium compound with a tetraalkoxysilane. The improvement comprises the use of a solvent mixture of an ether solvent and an inert hydrocarbon solvent in the second step of reaction between a polycyclic amido magnesium compound with a tetraalkoxysilane. If the reaction of the second step for preparing the di(polycyclic amino)dialkoxysilane is performed in an ether solvent alone or in an inert hydrocarbon solvent alone, the yield of di(polycyclic amino)dialkoxysilane lowers and thus the preparation process becomes disadvantageous from the viewpoint of an industrially applicable process.

DETAILED DESCRIPTION OF THE INVENTION

In the RMgX which stands for the organomagnesium compound, R represents a hydrocarbyl group, preferably having 1 to 24 carbon atoms, such as, methyl, ethyl, propyl, isopropyl, butyl, isobutyl, hexyl, octyl, phenyl, or benzyl. X represents a sigma-bonding ligand such as halogen, hydrocarbyloxy, hydrocarbylamide, or carboxy.

Examples of the organomagnesium compounds having the formula RMgX include alkylmagnesium chloride, alkylmagnesium bromide, alkylmagnesium iodide, alkylmagnesium methoxide, alkylmagnesium ethoxide, alkylmagnesium isopropoxide, and alkylmagnesium butoxide, in which the alkyl can be methyl, ethyl, propyl, butyl, hexyl, or octyl.

Since most organomagnesium compounds are stable in the form of an ether solution, they are generally present in an ether solvent in their production and storage. Examples of the ether solvents include dialkyl ethers such as diethyl ether, diisopropyl ether, dibutyl ether, and diisoamyl ether and cyclic ethers such as tetrahydrofuran, tetrahydropyran, and dioxane. Preferably, a dialkyl ether such as isopropyl ether is employed in combination with a cyclic ether such as tetrahydrofuran. In the combination, the volume ratio between dialkyl ether and cyclic ether preferably is in the range of 20:1 to 1:1 (dialkyl ether:cyclic ether). In the first step, the ether solvent can be employed in combination with an inert hydrocarbon solvent.

As describe hereinbefore, the second step of the process of the invention for the reaction between the polycyclic amido magnesium compound and tetraalkoxysilane is necessarily conducted in a mixture of an ether solvent and an inert solvent. If only one solvent (either an ether solvent or an inert hydrocarbon solvent) is employed in the second step, the reaction gives the desired di(polycyclic amino) dialkoxysilane only in a relatively low yield. Such low yield is unfavorable when the process is performed in industry. The volume ratio between an ether solvent and an inert hydrocarbon solvent preferably is in the range of 1:10 to 1:0.5(ether:hydrocarbon), more preferably in the range of 1:5 to 1:0.5.

Examples of the ether solvents are those described hereinbefore for the ether solvents of the first step.

Examples of the inert hydrocarbon solvents which are employable in combination with the ether solvent include pentane, hexane, heptane, octane, cyclohexane, mineral oil, benzene, toluene, and xylene. Preferred are hydrocarbon solvents having a low boiling point such as pentane, hexane and heptane.

The use of the hydrocarbon solvent in combination with the ether solvent in the second step is also advantageous for efficiently isolating the desired di(polycyclic amino) dialkoxysilane from a mixture of the di(polycyclic amino) dialkoxysilane and a by-produced magnesium alkoxide after the reaction of the second step is complete.

The secondary polycyclic amine compound to be employed in the process of the invention preferably is a secondary polycyclic perhydroamine compound. Examples of the secondary polycyclic perhydroamine compounds include perhydroindole, perhydroisoindole, perhydroquinoline, perhydroisoquinoline, perhydrocarbazole, perhydroiminostilbene, perhydroacrydine, amine compounds having a polycyclic ring fused with a cyclohexyl ring such as perhydrobenzo[f] quinoline, perhydrobenzo[g]quinoline, perhydrobenzo[g] isoquinoline and perhydrophenantolidine. Derivatives of these secondary polycyclic amine compounds in which one or more hydrogen atoms attached to a carbon atom of the amine compound are replaced with an alkyl group, a phenyl group, or a cycloalkyl group. Preferred are perhydroindole, perhydroisoindole, perhydroquinoline, perhydroisoquinoline, their derivatives having a substituent. The amine compound can be in the form of its cis or trans isomer.

Most amine compounds are hygroscopic. The secondary polycyclic amine compound to be employed in the process of the invention preferably has such low water content as not more than 1 weight %, more preferably not more than 0.1 weight %, most preferably not more than 0.03 weight %. Most amine compounds are easily oxidized in the presence of oxygen to get colored. In order to obviate the coloration, the oxygen contained in the reaction system is preferably removed, for instance, by replacing the oxygen with an inert gas such as nitrogen in advance of performing the reaction.

Examples of the tetraalkoxy silanes employed in the invention include tetramethoxysilane, tetraethoxysilane, tetrapropoxysilane, tetraisopropoxysilane, tetraisobutoxysilane, tetra-t-butoxysilane, and their mixtures. Most preferred is tetramethoxysilane.

The reaction between the organomagnesium compound and the secondary polycyclic amine compound in the first step is preferably conducted at a temperature of −30° C. to +100° C., most preferably −10° C. to +80° C., for a period of 1 to 360 minutes. The secondary polycyclic amine compound and the organomagnesium compound are generally employed in the reaction in a molar ratio of 20 to 0.05, preferably 3 to 0.1, more preferably 1 to 0.5, in terms of the amine compound/organomagnesium compound.

The reaction between the organomagnesium compound and the secondary polycyclic amine compound in the first step gives a polycyclic amido magnesium compound. Representative examples of the polycyclic amido magnesium compounds are polycyclic perhydroamido magnesium compounds.

In the second step, the polycyclic amido magnesium compound reacts with a tetraalkoxysilane to give the desired di(polycyclic amino)dialkoxysilane. In the reaction, a magnesium alkoxide is produced as a by-product in addition to the di(polycyclic amino)dialkoxysilane. The by-produced magnesium alkoxide is insoluble solid. Therefore, the by-product can be separated by filtration or centrifugal separation to give a filtrate or a mother liquor. The desired di(polycyclic amino)dialkoxysilane can be isolated from the filtrate or the mother liquor, for instance, by distillation.

In performing the second step, it is preferred that the tetraalkoxysilane is added to the polycyclic amido magnesium compound. The reaction is generally conducted at a temperature in the range of −20° C. to +140° C., preferably 0° C. to 100° C., for a period of 1 to 60 minutes. The polycyclic amido magnesium compound and the tetraalkoxysilane are generally employed in the reaction in a molar ratio of 20 to 0.1, preferably 5 to 0.5, in terms of the amido magnesium compound/tetraalkoxysilane. If the molar ratio of more than 1 is adopted, the reaction rate is accelerated. In this case, however, the loss of unreacted polycyclic amido magnesium compound increases. In the case that the polycyclic amido magnesium compound is expensive, the production cost increases. Therefore, the molar ratio of less than 1 is preferably adopted so as to reduce the production cost. In the reaction under such condition, a polycyclic amino trialkoxysilane is produced as by-product. The by-product can be recovered from the reaction mixture and may be employed in a reaction with the polycyclic amido magnesium compound to obtain the desired di(polycyclic amino) dialkoxysilane.

According to the invention, a di(polycyclic amino) dialkoxysilane, which is of value as an auxiliary catalyst component for polymerizing an α-olefin to produce an α-olefin polymer having a high stereoregularity and a broad molecular weight distribution can be easily produced in a high yield with little handling trouble.

The present invention is further described by the following Examples.

EXAMPLE 1

In a 1,000 mL volume flask equipped with a dropping funnel and a glass filter was placed a stirrer piece and then introduced a nitrogen gas using a vacuum pump. In the flask were then placed 100 mL of tetrahydrofuran, 300 mL of n-heptane and 53.7 g (0.36 mole) of perhydroisoquinoline (trans/cis=1/3.2). In the dropping funnel, 220 mL of an isopropyl ether solution containing 0.42 mole of butylmagnesium chloride was placed. The butylmagnesium chloride-containing isopropyl ether solution was dropwise introduced gradually into the flask at room temperature. The mixture in the flask was stirred at room temperature for one hour and further at 60° C. for 3 hours to give a reaction mixture. Subsequently, 27.4 g (0.18 mole) of tetramethoxysilane was placed in the vacant dropping funnel. The tetramethoxysilane was then dropwise added gradually to the reaction mixture in the flask. The mixture in the flask was stirred at 60° C. for 3 hours and further at 80° C. for 8 hours. In the course of performing the dropwise addition, 200 mL of the tetrahydrofuran/isopropyl ether mixed solvent was distilled off, and two portions of n-heptane (total volume: 200 mL) were added to the reaction mixture. The by-produced solid of methoxymagnesium chloride was removed by filtration. The filtrate was distilled to recover the desired di(perhydroisoquinolino)dimethoxysilane (ratio of isomers of trans-trans/trans-cis/cis-cis=approximately 6/36/58, b.p.: 181° C./1 mmHg). Gas chromatographic analysis indicated a purity of 96.6%. Yield was 90.7%.

EXAMPLE 2

The procedures of Example 1 were repeated except for employing 200 mL of tetrahydrofuran and 250 mL of n-heptane. The filtrate was distilled to give di(perhydroisoquinolino)dimethoxysilane (b.p.: 181° C./1 mmHg). Gas chromatographic analysis indicated a purity of 96.1%. Yield was 90.2%.

COMPARISON EXAMPLE 1

The procedures of Example 1 were repeated except for employing no tetrahydrofuran and 450 mL of n-heptane. The filtrate was distilled to give di(perhydroisoquinolino)dimethoxysilane (b.p.: 181° C./1 mmHg). Gas chromatographic analysis indicated a purity of 95.9%. Yield was 82.5%.

COMPARISON EXAMPLE 2

The procedures of Example 1 were repeated except for employing 450 mL of tetrahydrofuran and no n-heptane. To the reaction mixture containing by-produced solid of methoxymagnesium chloride was added 300 mL of n-heptane. The solid was then removed by filtration. The filtrate was distilled to give di(perhydroisoquinolino)dimethoxysilane (b.p.: 181° C./1 mmHg). Gas chromatographic analysis indicated a purity of 95.5%. Yield was 85.3%.

EXAMPLE 3

In a 1,000 mL volume flask equipped with a dropping funnel was placed a stirrer piece and then introduced a nitrogen gas using a vacuum pump. In the flask were then placed 35 mL of tetrahydrofuran, 185 mL of toluene and 50.8 mL (0.34 mole) of perhydroisoquinoline (trans/cis=1/3.2). In the dropping funnel, 211 mL of an isopropyl ether solution containing 0.357 mole of butylmagnesium chloride was placed. The butylmagnesium chloride-containing isopropyl ether solution was dropwise introduced gradually into the flask at room temperature. The mixture in the flask was stirred at room temperature for one hour and further at 60° C. for 3 hours to give a reaction mixture. Subsequently, 25.1 mL (0.17 mole) of tetramethoxysilane was placed in the vacant dropping funnel. The tetramethoxysilane was then dropwise added gradually to the reaction mixture (warmed at 60° C.) in the flask. The mixture in the flask was stirred at 85° C. for 8 hours. The by-produced solid of methoxymagnesium chloride was removed by filtration using a G4 glass filter. The filtrate was distilled to recover the desired di(perhydroisoquinolino)dimethoxysilane (ratio of isomers of trans-trans/trans-cis/cis-cis=approximately 6/36/58, b.p.: 181° C./1 mmHg). Gas chromatographic analysis indicated a purity of 96.6%. Yield was 90.7%.

EXAMPLE 4

The procedures of Example 3 were repeated except for employing 20 mL of tetrahydrofuran and 200 mL of toluene. The filtrate was distilled to give di(perhydroisoquinolino)dimethoxysilane (b.p.: 181° C./1 mmHg). Gas chromatographic analysis indicated a purity of 96.1%. Yield was 89.2%.

EXAMPLE 5

The procedures of Example 3 were repeated except for employing perhydroisoquinoline (trans/cis=1/1). The filtrate was distilled to give di(perhydroisoquinolino)dimethoxysilane (b.p.: 181° C./1 mmHg). Gas chromatographic analysis indicated a purity of 96.8%. Yield was 91.3%.

EXAMPLE 6

The procedures of Example 3 were repeated except for employing 162 mL of an n-butyl ether solution containing 0.357 mole of butylmagnesium chloride in place of the butylmagnesium chloride-containing isopropyl ether solution. The filtrate was distilled to give di(perhydroisoquinolino)dimethoxysilane (b.p.: 181° C./1 mmg). Gas chromatographic analysis indicated a purity of 94.9%. Yield was 88.8%.

COMPARISON EXAMPLE 3

The procedures of Example 3 were repeated except for employing no tetrahydrofuran and 220 mL of toluene. The filtrate was distilled to give di(perhydroisoquinolino)dimethoxysilane (b.p.: 181° C./1 mmHg). Gas chromatographic analysis indicated a purity of 95.9%. Yield was 81.6%.

COMPARISON EXAMPLE 4

The procedures of Example 1 were repeated except for employing 220 mL of tetrahydrofuran and no toluene. To the reaction mixture containing by-produced solid of methoxymagnesium chloride was added 100 mL of n-heptane. The solid was then removed by filtration. The filtrate was distilled to give di(perhydroisoquinolino)dimethoxysilane (b.p.: 181° C./1 mmHg). Gas chromatographic analysis indicated a purity of 95.46. Yield was 78.4%.

What is claimed is:

1. A process for preparing a di(polycyclic amino) dialkoxysilane which comprises the steps of:
    reacting a secondary polycyclic-amine compound with an organomagnesium compound having a formula of RMgX, wherein R is a hydrocarbyl group and X is a sigma-bonding ligand, in an ether solvent, to produce a polycyclic-amido magnesium compound, and
    reacting the polycyclic-amido magnesium compound with a tetraalkoxysilane in a solvent mixture of an ether solvent and an inert hydrocarbon solvent.
2. The process for preparing a di(polycyclic amino) dialkoxysilane according to claim 1, wherein the solvent mixture comprises an ether solvent and an inert hydrocarbon solvent in a volume ratio in the range of 1:10 to 1:0.5.

3. The process for preparing a di(polycyclic amino) dialkoxysilane according to claim 1, wherein the ether solvent for the reaction between the secondary polycyclic-amine compound and the organsmagnesium compound is a mixture of a dialkyl ether and a cyclic ether.

4. The process for preparing a di(polycyclic amino) dialkoxysilane according to claim 1, wherein the ether solvents for the reaction between a secondary polycyclic amine compound and an organomagnesium compound and of the solvent mixture are selected from the group consisting of diethyl ether, diisopropyl ether, dibutyl ether, diisoamyl ether, tetrahydrofuran, tetrahydropyran, and dioxane.

5. The process for preparing a di(polycyclic amino) dialkoxysilane according to claim 1, wherein the inert hydrocarbon solvent is selected from the group consisting of pentane, hexane, heptane, octane, cyclohexane, mineral oil, benzene, toluene, and xylene.

6. The process for preparing a di(polycyclic amino) dialkoxysilane according to claim 1, wherein R of the organomagnesium compound is selected from the group consisting of methyl, ethyl, propyl, isopropyl, butyl, isobutyl, hexyl, octyl, and phenyl.

7. The process for preparing a di(polycyclic amino) dialkoxysilane according to claim 1, wherein X of the organomagnesium compound is selected from the group consisting of halogen, hydrocarbyloxy, hydrocarbylamide, and carboxyl.

8. The process for preparing a di(polycyclic amino) dialkoxysilane according to claim 1, wherein the secondary polycyclic amine compound is a secondary polycyclic perhydro-amine compound.

9. The process for preparing a di(polycyclic amino) dialkoxysilane according to claim 8, wherein the secondary polycyclic perhydro-amine compound is perhydroquinoline, perhydroisoquinoline, or its derivative having a substituent of alkyl, phenyl, or cycloalkyl on its carbon atom.

* * * * *